(12) United States Patent
Pendergast et al.

(10) Patent No.: US 6,348,589 B1
(45) Date of Patent: Feb. 19, 2002

(54) CERTAIN DINUCLEOTIDES AND THEIR USE AS MODULATORS OF MUCOCILIARY CLEARANCE AND CILIARY BEAT FREQUENCY

(75) Inventors: William Pendergast, Durham; Benjamin R. Yerxa, Raleigh; Janet L. Rideout, Raleigh; Suhaib M. Siddiqi, Raleigh, all of NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/101,395

(22) PCT Filed: Feb. 6, 1998

(86) PCT No.: PCT/US98/02702

§ 371 Date: Jul. 13, 1998

§ 102(e) Date: Jul. 13, 1998

(87) PCT Pub. No.: WO98/34942

PCT Pub. Date: Aug. 13, 1998

Related U.S. Application Data

(63) Continuation-in-part of application No. 08/798,508, filed on Feb. 10, 1997, now Pat. No. 5,900,407, which is a continuation-in-part of application No. 08/797,472, filed on Feb. 6, 1997.

(51) Int. Cl.$^7$ .......................... C07H 21/00; A61K 31/70
(52) U.S. Cl. ...................... 536/25.6; 536/26.1; 514/47; 514/48; 514/51
(58) Field of Search .............................. 514/47, 48, 51; 536/25.6

(56) References Cited

U.S. PATENT DOCUMENTS

| | | | |
|---|---|---|---|
| 4,855,304 A | 8/1989 | Devash | 514/47 |
| 5,292,498 A | 3/1994 | Boucher | 424/45 |
| 5,789,391 A | * 8/1998 | Jacobus et al. | 514/51 |
| 5,837,861 A | * 11/1998 | Pendergast et al. | 536/25.6 |

FOREIGN PATENT DOCUMENTS

| | | |
|---|---|---|
| WO | WO 96/02554 | 2/1996 |
| WO | WO 96 02554 A | 2/1996 |
| WO | WO 96 40059 A | 12/1996 |
| WO | WO 96/40059 | 12/1996 |
| WO | WO 98 03177 A | 1/1998 |
| WO | WO 9803182 A | 1/1998 |
| WO | WO 98 15563 | 4/1998 |

OTHER PUBLICATIONS

Hagemeier, E., et al., "High–performance liquid chromatographic method for separation of dinucleotides," *Journal of Chromotography* 237:174–177 (1982).

Hata, T., et al., "The Synthesis of α,γ–Dinucleoside Triphosphates the Confronted Nucleotide Structure Found at the Terminus of Eukaryote Messenger Ribonucleic Acid," *Chemistry Letters*, pp. 987–990 (1976).

Holler, E. et al., "Circular Dichroism and Ordered Structure of Bisnucleoside Oligophosphates and their $Zn^{2+}$ and $Mg^{2+}$ Complexes," *Biochemistry* 22:4924–4933 (1983).

Huhn, G., et al., "Purification of Nucleoside–5'–diphosphates: A New Ion–Exchange Method" *Separation Science and Technology* 28(11 & 12):1959–1970 (1993).

Orr, R.M., et al., "Inhibition of Human Leukaemic Thymidylate Kinase and L1210 Ribonucleotide Reductase By Dinucleotides of Adenosine and Thymidine and Their Phosphonate Analogues," *Biochemical Pharmacology*, 37(4): 673–677, (1988) XP– 002092439.

Pintor, J., et al., "Dopamine Receptor Blockade Inhibits the Amphetamine–Induced Release of Diadenosine Polyphosphates, Diadenosine Tetraphosphate and Diadenosine Pentaphosphate, from Neostriatum of the Conscious Rat," *Journal of Biochemistry* pp. 9716–9727 (1996).

Plateau, P., et al., "Catabolism of Bis(5'–nucleosidyl) Oligophosphates in *Escherichia coli*: Metal Requirements and Substrate Specificity of Homogeneous Diadenosine–5', 5''–$P^1$, $P^4$–tetraphosphate Pyrophosphohydrolase," *Biochemistry*, 24:914–922, (1985) XP–002092441.

Scheffzek, K., "Crystal Structure of the Complex of UMP/CMP Kinase from *Dictyostelium discoideum* and the Bisubstrate Inhibitor $P^1$–(5' –Adenosyl) $P^5$–(5' –Uridyl) Pentaphosphate ($UP_5A$) and $Mg^{+2}$ at 2.2Å Implications for Water –Mediated Specificity," *Biochemistry*, 35(30):9716–9727, (1996) XP–002092444.

Stepinski, J., et al., "Synthesis and Properties of $P^{1,}P^2$–, $P^1,P^3$–And $P^1,P^4$–Dinocleoside D1–, Tri– and Tetraphosphate mRNA 5'–Cap Analogues," *Nucleosides & Nucleotides* 14(3–5):717–721 (1995).

Stridh, S., et al., "Functional Analysis of Influenza RNA Polymerase Activity by the Use of Caps, Oligonucleotides and Polynucleotides," *Antiviral Research*, 1(2):97–105, (1981)XP–002092446.

(List continued on next page.)

Primary Examiner—Gary Geist
Assistant Examiner—Howard V. Owens
(74) Attorney, Agent, or Firm—Albert P. Halluin; Viola T. Kung; Howrey Simon Arnold & White, LLP

(57) ABSTRACT

The present invention relates to certain novel dinucleotides and formulations thereof which are highly selective agonists of the $P2Y_2$ and/or $P2Y_4$ purinergic receptor. They are useful in the treatment of chronic obstructive pulmonary diseases such as chronic bronchitis, PCD, cystic fibrosis, as well as prevention of pneumonia due to immobility. Furthermore, because of their general ability to clear retained mucus secretions and stimulate ciliary beat frequency, the compounds of the present invention are also useful in the treatment of sinusitis, otitis media and nasolacrimal duct obstruction. They are also useful for treatment of dry eye disease and retinal detachment.

9 Claims, No Drawings

OTHER PUBLICATIONS

Tarusova, N., et al., "Organophosphorus Analogs of Biologically Active Compounds. XVI. Comparison of the optical properties of zinc II complexes of $P^1$, $P^4$–bis(5' –adenosyl) tetraphosphate and its phosphonate analogs," *Chemical Abstracts*, 110(17) (Apr. 1989) XP–002092449.

Theoclitou, M., et al., "Characterisation of stress protein LysU. Enzymic synthesis of diadenosine 5', 5"–$P^1$, $P^4$–tetraphosphate ($Ap^4A$) analogs by LysU," *Journal of the Chemical Society, Perkin Transactions* 1(16):2009–2019, (Aug. 1996) XP–002092434.

Tumanov, Y., et al., "Chemical Synthesis of Nucleoside–5'–Polyphospho–5'–Nucleosides," *Chemical Abstracts*, 109(1): (Jul., 1988) XP–002092450.

Visscher, J. et al., "Selective cleavage of pyrophosphate linkages," *Nucleic Acids Res.* 20(21):5749–5752 (1992).

Blackburn, G.M., et al., "Synthesis, Physical, Chemical, and Enzyme Studies on Bis–2,6–Diaminopurine β–D–Ribofuranoside $P^1$, $P^4$–Tetraphosphate." *Nucleosides and Nucleotides*, 10(1–3):549–551 (1991) XP–002092448.

Chavan, A.J., et al., "Identification of N–Terminus Peptide of Human Granulocyte/Macrophage Colony Stimulating Factor as the Site of Nucleotide Interaction." *Biochemical and Biophysical Research Communications*, 208(1):390–396, (1995) XP–002092442.

Guarnowski, A., et al., "Methylene and Halomethylene Analogues of Diadenosine 5', 5"–$P^1$, $P^3$–Triphosphate (ApppA) As Substrates or Inhibitors of ApppA–Degrading Enzymes.", *Nucleosides and Nucleotides*, 14(3–5):731–734 (1995) XP–002092438.

Hagemeier, E., et al., "High–Performance Liquid Chromatographic Method for Separation of Dinucleotides." *Journal of Chromatography*, 237(1):174–177 (1982), XP–002092443.

Hata, T., et al., "The Synthesis of alpha, gamma–Dinucleoside Triphosphates : The Confronted Nucleotide Structure Found at the 5'–Terminus of Eukaryote Messenger Ribonucleic Acid." *Chemistry Letters*, 987–990, (1976), XP–002093657.

Holler, E., et al., "Circular Dichroism and Ordered Structure of Bisnucleoside Oligophosphates and Their $Zn^{2+}$ and $Mg^{2+}$ Complexes." *Biochemistry*, 22:4924–4933, (1983) XP–002092437.

Huhn, G.F., et al., "Purification of Nucleoside–5'–diphosphates : A New Ion–Exchange Method." *Separation and Science Technology*, 28(11&12):1959–1970, (1993) XP–002093658.

Nuutinen, J., "Activation of the Impaired Nasal Mucociliary Transport in Children: Preliminary Report" *International Journal of Pediatric Otorhinolaryngology*, 10(1):47–52, (1985), XP–000654070.

Ono, K., et al., "Inhibitory Effects of Diadenosine Polyphosphates and Diguanosine Polyphosphates on Terminal Deoxynucleotidyltransferase from Calf Thymus." *Biomedicine*, 36(10):414–419, (1982).

Orr, R.M., et al., "Inhibition of Human Leukaemic Thymidylate Kinase and L1210 Ribonucleotide Reductase By Dinucleotides of Adenosine and Thymidine and Their Phosphonate Analogues." *Biochemical Pharmacology*, 37(4): 673–677, (1988) XP– 002092439.

Pintor, J., et al., "Diinosine Polyphosphates, a Group of Dinucleotides with Antagonistic Effects on Diadenosine Polyphosphate Receptor." *Molecular Pharmacology*, 51(2):277–284, (1997) XP–002092447.

Plateau, P., et al., Catabolism of Bis(5'–nucleosidyl) Oligophosphates in *Escherichia coli* : Metal Requirements and Substrate Specificity of Homogeneous Diadenosine–5', 5"–$P^1$, $P^4$–tetraphosphate Pyrophosphohydrolase, *Biochemistry*, 24:914–922, (1985) XP–002092441.

Stridh, S., et al., "Functional Analysis of Influenza RNA Polymerase Activity by the Use of Caps, Oligonucleotides and Polynucleotides." *Antiviral Research*, 1(2):97–105, (1981)XP–002092446.

Tarusova, N.B., et al., "Organophosphorus Analogs of Biologically Active Compounds. XVI. Comparison of the optical properties of zinc II complexes of $P^1$, $P^4$–bis(5' –adenosyl)tetraphosphate and its phosphonate analogs." *Chemical Abstracts*, 110(17) (Apr. 1989) XP–002092449.

Theoclitou, M.E., et al., "Characterisation of stress protein LysU. Enzymic synthesis of diadenosine 5' 5"–$P^1$, $P^4$–tetraphosphate ($Ap^4A$) analogs by LysU." *Journal of the Chemical Society, Perkin Transactions* 1(16):2009–2019, (Aug. 1996) XP–002092434.

Tumanov, Y.V., et al., "Chemical Synthesis of Nucleoside–5'–Polyphospho–5'–Nucleosides." *Chemical Abstracts*, 109(1): (Jul., 1988) XP–002092450.

Baker, J.C., et al., "Alterations in levels of 5'–adenyl dinucleotides following DNA damage in normal human fibroblasts and fibroblasts derived from patiente with xeroderma pigmentosum" *Mutation Res.*, 208, 87 (1988).

Blackburn, G.M., et al., "Synthesis, Physical, Chemical, and Enzyme Studies on Bis–2,6–Diaminopurine β–D–Ribofuranoside $P^1,P^4$–Tetraphosphate" *Nucleosides & Nucleotides*, 10, 549 (1991).

Bone, R., et al., "Inhibition of Adenosine and Thymidylate Kinases by Bisubstraate Analogs" *J. Biol. Chem.*, 261, 16410 (1986).

Brown, H. et al., "Evidence that UTP and ATP Regulate Phospholipase C through a Common Extracellular 5'–Nucleotide Receptor in Human Airway Epithelian Cells" *Mol. Pharmacol.* 40, 648–55 (1991).

Casillas, T., et al., "Kinetic and Allosteric Cooperativity in L–Adenosine Transport in Chromaffin Cells. A Mnemonical Transporter" *Biochemstry*, 32, 14203 (1993).

Castro, E., et al., "Effect of diadenosine polyphosphates on catecholamine secretion from isolated chromaffin cells" *Br. J. Pharmacol.*, 100, 360 (1990).

Castro, E., et al., "Single–cell fura–2 microfluorometry reveals different purinoceptor subtypes coupled to $Ca^{2+}$ influx and intracellular $Ca^{2+}$ release in bovine adrenal chromaffin and endothelial cells" *Pflugers Arch.*, 426, 524 (1994).

Castro, E., et al., "$Ca^{2+}$–stores mobilization by diadenosine tetraphosphate, $Ap_4A$, through a putative $P_{2Y}$ purinoceptor in adrenal chromaffin cells" *Br. J. Pharmacol.*, 106, 833 (1992).

Castro, E., et al., "Cell–specific Purinergic Receptors Coupled to $Ca^{2+}$Entry and $Ca^{2+}$Release from Internal Stores in Adrenal Chromaffin Cells" *J. Biol. Chem.*, 270, 5098 (1995).

Coste, H. et al., "Non–adenylylated Bix(5'–nucleosidyl1) Tetraphosphates Occur in *Saccharomyces cerevisiae* and in *Escherichia coli* and Accumulate upon Temperature Shift of Exposure to Cadmium" *J. Biol. Chem.*, 262, 12096 (1987).

Ding, P.Z., et al., "Oligomerization of Uridine Phosphorimidazolides on Montmorillonite: a Model for the Prebiotic Synthesis of RNA on Minerals" *Chemical Abstracts*, 125; No. (19) 435, XP002073684, (1996).

Drutz, D. et al., "Uridine 5' Triphosphate (UTP) Regulates Mucociliary Clearance Via Purinergic Receptor Activation" *Drug Dev. Res.* 37(3), 185 (1996).

Elmaleh, D.R., et al., "$^{99m}$Tc–labeled nucleotides as tumor–seeking radiodiagnostic agents" *Proc. Natl. Acad. Sci.*, 81, 918 (1984).

Gobran, L., "$P_{2u}$ purinoceptor stimulation of surfactant secretion coupled to phosphatidylcholine hydrolysis in type II cells" *Am. J. Physiol.* 267, L625–L633 (1994).

Grummt, F., "Diadenosine tetraphosphate ($Ap_4A$): a putative chemical messenger of cell proliferation control and inducer of DNA replication" et al., *Plant Mol. Bio.*, 2, 41 (1983).

Guranowski, A., "Synthesis of Diadenosine 5',5"–$P^1$, $P^4$–Tetraphosphate (ApppA) from Adenosine 5'–Phosphosulfate and Adenosine 5'–Triphosphate Catalyzed by Yeast ApppA Phosphorylase" et al., *Biochemistry*, 27, 2959 (1988).

Hiderman, R.H., "Identification of a Unique Membrane Receptor for Adenosine 5',5"–P1,P4–Tetraphosphate" et al., *J. Biol. Chem.*, 266, 6915 (1991).

Kanavarioti, A., et al., "Unexpectedly Facile Synthesis of Symmetrical $P^1,P^2$–Dinucleoside–5'pyrophosphates" *Tett. Lett.*, 32, 6065 (1991).

Kim, B.K., "Antithrombotic effect of $\beta,\beta'$–monochloromethylene diadenosine 5',5"–$P^1,P^4$–tetraphosphate" et al., *Proc. Natl. Acad. Sci.*, 89, 11056 (1992).

Kimura, T., et al., "Disposition of Diadenosine 5',5"–$P^1$, $P^4$–Tetraphosphate (Ap4A) in Rates" *Biol. Pharm. Bull.*, 18, 1556 (1995).

Klein, G., et al., "Methylenediphosphonate, a Metabolic Poison in *Dictyostelium discoideum*. $^{31}$P NMR Evidence for Accumulation of Adenosine 5'($\beta\gamma$–Methylenetriphosphate) and Diadenosine 5',5"–$P^2,P^3$–Methylenetetraphosphate)" *Biochemistry*, 27, 1897 (1988).

Klein, J. "Otitis Media" *Clin. Infect. Dis.* 19, 823–33 (1994).

Knowles, M. et al., "Activation by Extracellular Nucleotides of Chloride Secretion in the Airway Epithelia of Patients with Cystic Fibrosis" *N. Engl. J. Med.* 325, 533–38 (1991).

Lazarowski, E., "Pharmacological selectivity of the clones human $P_{2u}$–purinoceptor: potent activation by diadenosine tetraphosphate" et al., *Brit. J. Pharm.*, 116, 1619–27 (1995).

Lethem, M. et al., "Nucleotide Regulation of Goblet Cells in Human Airway Epithelian Explants; Normal Exocytosis in Cystic Fibrosis" *Am. J. Respir. Cell Mol. Biol.* 9, 315–22 (1993).

Lobaton, C.D., et al., "Diguanosinetetraphosphatase from Rat Liver: Activity on Diadenosine tetraphosphate and Inhibition by Adenosine Tetraphosphate" *Eur. J. Biochem.*, 50, 495 (1985).

Lowe, G., et al., "Stereochemical Analysis of the Enzymic Synthesis and Hydrolysis of $Ap_4A$" *Nucleosides & Nucleotides*, 10, 181 (1991).

Luthje, J., et al., "Catabolism of $Ap_4A$ and $Ap_3A$ in whole blood" *Eur. J. Biochem.*, 173, 241 (1988).

Mason, S. et al., "Regulation of transepithelian ion transport and intracellular calcium by extracellular ATP in human normal and cystic fibrosis airway epithelium" *Br. J. Pharmacol.* 103, 1649–56 (1991).

McLennan, A.G., et al., "Diadenosine 5',5"–$P^1$, $P^4$–tetraphosphate in developing embryos of Artemia" *Nucleic Acid Res.*, 12, 1609 (1984).

Miras–Portugal., M.T., et al., "Characterization of Ectonucleotidases in Chromaffin Cells" *Ann. NY Acad. Sci.*, 603, 523 (1990).

Morii, H., et al., "Adenosine(5')hexaphospho(5')adenosine stimulation of a $Ca^{2+}$–induced $Ca^{2+}$–release channel from skeletal muscle sarcoplasmic reticulum" *Eur. J. Biochem.*, 205, 979 (1992).

Moss A. and V. Parsons, "Current Estimates From the National Health interview Survey" *National Center for Health Statistics*, 1986:66–7, DHHS Publication No. (PHS) 86–1588 (1985).

Ng, K.E. et al., "The action of a water–soluable carbodiimide and adenosine–5'–polyphasphates" *Nucleic Acid Res.*, 15, 3573 (1987).

Olivier, K. et al., "Acute Safety and Effects on Mucociliary Clearance of Aerosolized Uridine 5'–Triphosphate +/–Amiloride in Norman Human Adults" *Am. J. Respr. Crit. Care Med.* 154, 217–23 (1996).

Panchenko, V.A., et al., "Diadenosine Polyphosphates Selectively Potentiate N–Type $Ca^{2+}$ Channels in Rat Central Neurons" *Neuroscience*, 70, 353 (1996).

Pintor, J., et al., "Dopamine Receptor Blockade Inhibits the Amphetamine–Induced Release of Diadenosine Polyphosphates, Diadenosine Tetraphosphate and Diadenosine Pentaphosphate, from Neostriatum of the Conscious Rat" *J. Neurochem.*, 64, 670 (1995).

Pintor, J. et al., "$P_2$ Purinergic Receptors for Diadenosine Polyphosphates in the Nervous System" *Gen. Pharmac.*, 26, No. 2, 229–235 (1995).

Pintor, J., et al., "A novel receptor for diadenosine polyphasphates coupled to calcium increase in rat midbrain synaptosomes" *Br. J. Pharmacol.* 115, 895 (1995).

Rapaport, E., et al., "HeLa cell DNA polymerase αis tightly associated with tryptophanyl–tRNA synthetase and diadenosine 5',5"–$P^1$, $P^4$–tetraphosphate binding activities" *Proc. Natl. Acad. Sci.*, 78, 838 (1981).

Rotilan, P., et al., "Di(1,$N^6$–ethenoadenosine)5', 5"–$P^1$, $P^4$–tetraphosphate, a fluorescent enzymatically active derivative of $Ap_4A$" *FEBS*, 280, 371 (1991).

Schulze–Lohoff, E., et al., "Vasoactive Diadenosine Polyphosphates Promote Growth of Cultured Renal Mesangial Cells" *Hypertension*, 26, 899 (1995).

Schlüter, H., et al., "Diadenosine phosphataes and the physiological control of blood pressure" *Nature*, 367, 186 (1994).

Sillero, M.A.G. et al., "Dinucleosidetriphosphatase from Rat Liver" *Eur. J. Biochem.*, 76, 331 (1977).

Silverman, R.H., et al., "The Search for Guanosine Tetraphosphate (ppGpp) and Other Unusual Nucleotides in Eucaryotes" *Microbiological Rev.*, 43, 27 (1979).

Stepinski, J., et al., "Synthesis and Properties of $P^1,P^2$–,$P^1$, $P^3$–and $P^1,P^4$–Dinucleoside DI, Tri– and Tetraphosphate mRNA 5'–Cap Analogues" *Nucleosides & Nucleotides*, 14, 717 (1995).

Vallejo, C.G., et al., "Dinucleosidasetetraphosphatase in Rat Liver and *Artemia salina*" *Biochem. Biophy. Acta*, 483, 304 (1976).

Visscher, J., et al., "Selective cleavage of pyrophosphate linkages" *Selective Cleavage of Pyrophosphate Linkages. Nucleic Acids Research*, 20, No. (21), 5749–5752, XP002073879, (1992).

Walker, J., et al., "The Adenosine 5',5",$P_1$, $P_4$–Tetraphosphate Receptor Is at the Cell Surface of Heart Cells" *Biochemistry*, 32, 14009 (1993).

Zamecnik, P.C., et al., "Analogues of diadenosine 5',5"–P$^1$, P$^4$–tetraphosphate (Ap,A) as potential anti–platelet–aggregation aagents" *Proc. Natl. Acad. Sci.*, 89, 2370 (1992).

Zamecnik, P., et al., "Diadenosine 5',5"–P$^1$, P$^4$–Tetraphosphate (Ap$_4$A): Its Roots in Cellular Metabolism[1]" *Analytical Biochem.*, 134, 1 (1983).

Zatorski, A., et al., "Chemical Synthesis of Benzamide Adenine Dinucleoide: Inhibition of Inosine Monophosphate Dehydrogenase (Types I and II)[1]", *Journal of Medicinal Chemistry*, 39, 2422–2426, XP002073881, (1996).

* cited by examiner

CERTAIN DINUCLEOTIDES AND THEIR USE AS MODULATORS OF MUCOCILIARY CLEARANCE AND CILIARY BEAT FREQUENCY

This application is a 371 of PCT/US98/02702 filed Feb. 6, 1998 which is cont-in-part of Ser. No. 08/797,472 filed Feb. 6, 1997 which is a continuation-in-part application of U.S. Ser. No. 08/798,508 filed Feb. 10, 1997, now U.S. Pat. No. 5,900,407.

TECHNICAL FIELD

This invention relates to certain dinucleotides which increase the hydration of retained mucus secretions, stimulate the production of mucins and increase ciliary beat frequency to increase clearance of retained secretions.

BACKGROUND OF THE INVENTION

Chronic obstructive pulmonary disease (COPD) affects 15 million patients in the U.S. and is the sixth leading cause of death. It is characterized by the retention of mucus secretions in the lungs. Many patients diagnosed with COPD have a disorder called chronic bronchitis (CB), and 600,000 patients are hospitalized each year due to an acute exacerbation of CB. Cystic fibrosis and Primary Ciliary Dyskinesia (PCD) are other examples of lung disorders which assume a clinical profile similar to COPD. Ciliary dyskinesia, whether primary or secondary, results in retained secretions that can only be cleared by coughing.

Another disease state characterized by the accumulation of retained mucous secretions is sinusitis. Sinusitis is an inflammation of the paranasal sinuses typically associated with an upper respiratory infection. It is this country's most common health-care complaint, affecting an estimated 31 million people. (A. Moss and V. Parsons, National Center for Health Statistics, 1986: 66–7, DHHS Publication No. (PHS) 86–1588 (1985)).

Otitis media (OM) is a viral or bacterial infection of the middle ear which primarily afflicts children under the age of three. It is usually precipitated by an upper respiratory infection which spreads into the middle ear via the nasopharynx and eustachian tube. Approximately 25–50 million office visits are made each year for diagnosis and treatment of OM. By age three, about 75% of children will have had at least one episode of acute OM (J. Klein, *Clin. Infect. Dis.* 19, 823–33 (1994)). Following appropriate treatment with antibiotics, accumulated fluid in the middle ear remains, causing hearing impairment and potential language and cognitive development delays. Enhanced ability to clear secretions in the middle ear would reduce or eliminate significant sequelae of otitis media.

An additional disorder resulting from retained secretions is pneumonia. Patients who are immobilized for a variety of reasons are at high risk for developing pneumonia. Despite extra vigilance and numerous interventions, pneumonia develops in over 400,000 patients per year, with significant morbidity and mortality.

There are also situations where it is therapeutically desirable to increase drainage of the lacrimal system. When the lacrimal drainage system is not functioning properly the result can be excessive tearing (epiphora), mucopurulent discharge, and recurrent dacryocystitis. Current treatments for nasolacrimal duct obstruction are mostly invasive surgical procedures, and researchers have sought to discover noninvasive pharmaceutical treatments.

Tear secretion can be stimulated from lacrimal accessory tissues via $P2Y_2$ and/or $P2Y_4$ purinergic receptor-mediated mechanisms similar to those which hydrate airway epithelia. Dry eye disease is the general term for indications produced by abnormalities of the precorneal tear film characterized by a decrease in tear production or an increase in tear film evaporatioin, together with the ocular surface disease that results. Currently, the pharmaceutical treatment of dry eye disease is mostly limited to administration of artificial tears (saline solution) to temporarily rehydrate the eyes. However, relief is short lived and frequent dosing is necessary.

Normally, mucous secretions are removed via the mucociliary clearance (MCC) system. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus.

It is now known that nucleoside phosphates such as uridine 5'-triphosphate (UTP) modulate all of the components of the MCC system. First, UTP has been shown to increase both the rate and total amount of mucin secretion by goblet cells in vitro (M. Lethem, et al., *Am J Respir. Cell Mol. Biol* 9, 315–22 (1993)). Second, UTP has been shown to increase cilia beat frequency in human airway epithelial cells in vitro (D. Drutz, et al., *Drug Dev. Res.* 37(3), 185 (1996)). And third, UTP has been shown to increase $Cl^-$ secretion, and hence, water secretion from airway epithelial cells in vitro (S. Mason, et al., *Br. J Pharmacol.* 103, 1649–56 (1991)). In addition, it is thought that the release of surfactant from Type II alveolar cells in response to UTP (Gobran, *Am. J. Physiol* 267, L625–L633 (1994)) contributes to optimal functioning of the lungs and may assist in maximizing MCC (M. Knowles, et al., *N. Engl. J. Med.* 325, 533–38 (1991)). UTP has been shown to increase intracellular $Ca^{++}$ due to stimulation of phospholipase C by the $P2Y_2$ receptor (H. Brown, et al., *Mol. Pharmacol* 40, 648–55 (1991)).

UTP's modulation of all components of the mucociliary escalator system results in a 2.5-fold improvement in lung mucociliary clearance in normal volunteers without any significant side-effects (K. Olivier, et al., *Am J. Respir. Crit. Care Med.* 154, 217–23 (1996)). In addition, UTP significantly enhanced cough clearance (clearance of retained secretions by coughing) in patients with PCD (P. Noone, et al., *Am. J. Respir. Crit. Care Med.* 153, A530 (1996)).

Because of UTP's demonstrated ability to increase the clearance of retained mucous secretions, applicants were motivated to investigate whether other nucleoside phosphates could be equally, if not more, therapeutically effective. The present invention is based upon this investigation.

Previously described dinucleotides are listed in Table I, along with their corresponding literature references.

TABLE I

DINUCLEOTIDES IN THE LITERATURE
(numbers in parentheses correspond to references that follow)

| $Np_2N$ | $Np_2N'$ | $Np_3N$ | $Np_3N'$ | $Np_4N$ | $Np_4N'$ |
|---|---|---|---|---|---|
| $Ap_2A$ (4, 1) | $Ap_2NAD$ (6) | $Up_3U$ (1) | $Ap_3T$ (20) | $Up_4U$ (2, 3) | $Ap_4U$ (3) |
| $Gp_2G$ (5, 1) | $Ap_2TAD$ (6) | $Ap_3A$ (1, 4, 29) | $m^7Gp_3G$ (5) | $Ap_4A$ (1, 4, 29) | $Ap_4C$ (3) |
| $m^7Gp_2m^7G$ (5) | $Ap_2C\text{-}NAD$ (6) | $Xp_3X$ (1) | $m^{2,2,7}Gp_3G$ (5) | $Cp_4C$ (3) | $Ap_4G$ (3) |
| | $Ap_2C\text{-}PAD$ (6) | $m^7Gp_3m^7G$ (5) | $m^{2,7}Gp_3G$ (5) | $Gp_4G$ (1, 5) | $Gp_4U$ (3) |
| | $Ap_2BAD$ (6) | $Gp_3G$ (1) | | $Xp_4X$ (1) | $Gp_4C$ (3) |
| | $m^7Gp_2G$ (5) | | | $Dp_4D$ (15) | $Up_4C$ (3) |
| | $Up_2U$ (43) | | | $eAp_4eA$ (7) | $Ap_4T$ (20) |
| | | | | $m^7Gp_4m^7G$ (5) | $m^7Gp_4G$ (5) |
| | | | | | $m^{2,7}Gp_4G$ (5) |
| | | | | | $m^{2,2,7}Gp_4G$ (5) |

| $Np_5N$ | $Np_5N'$ | $Np_6N$ | $Np_6N'$ | $Np_8N$ |
|---|---|---|---|---|
| $Ap_5A$ (4) | $Ap_5T$ (20) | $Ap_5A$ (4) | $Ap_6T$ (20) | $Ap_3A$ (4) |

| AppZppA | DppZppD | ApZppZpA | ApSpZpSpA |
|---|---|---|---|
| Z | Z | Z | Z |
| $CH_2$ (8) | $CH_2$ (15) | $CH_2$ (8) | CHF (8) |
| $CH_2CH_2$ (8) | $CH_2CH_2$ (15) | $CH_2CH_2$ (8) | $CF_2$ (8) |
| CHF (8) | CHF (15) | CHF (8) | O (8) |
| $CF_2$ (8) | $CF_2$ (15) | $CF_2$ (8) | |
| CHCl (8) | CHCl (15) | CHCl (8) | |
| $CCl_2$ (8) | $CCl_2$ (15) | $CCl_2$ (8) | |

A = Adenosine
U = Uridine
G = Guanosine
T = Thymidine
X = Xanthosine
TAD = Tiazofurin
BAD = Benzamide riboside
D = 2,6-Diaminopurine
eA = Ethenoadenosine
$m^7G$ = 7-Methylguanosine
$m^{2,7}G$ = 2,7-Dimethylguanosine
$m^{2,2,7}G$ = 2,2,7-Trimethylguanosine
NAD = nicotinamide riboside
C-NAD = C-nicotinamide riboside
C-PAD = C-picolinamide riboside
N = Nucleoside (1) M. A. G. Sillero et al., Eur. J. Biochem., 76, 331 (1997)
(2) C. G. Vallejo et al., Biochim. Biophys. Acta, 483, 304 (1976)
(3) H. Coste et al., J. Biol. Chem., 262, 12096 (1987)
(4) K. E. Ng et al., Nucleic Acid Res., 15, 3573 (1987)
(5) J. Stepinski et al., Nucleosides & Nucleotides, 14, 717 (1995)
(6) A. Zatorski et al., J. Med. Chem., 39, 2422 (1996)
(7) P. Rotilan et al., FEBS, 280, 371 (1991)
(8) P.C. Zamecnik et al., Proc. Natl. Acad. Sci., 89, 2370 (1992)
(9) J. Walker et al., Biochemistry, 32, 14009 (1993)
(10) R. H. Hiderman et al., J. Biol. Chem., 266, 6915 (1991)
(11) J. Luthje et al., Eur. J. Biochem., 173, 241 (1988)
(12) R. H. Silverman et al., Microbiological Rev., 43, 27 (1979)
(13) C. D. Lobaton et al., Eur. J. Biochem., 50, 495 (1975)
(14) G. Lowe et al., Nucleosides & Nucleotides, 10, 181 (1991)
(15) G. M. Blackburn et al., Nucleosides & Nucleotides, 10, 549 (1991)
(16) J. C. Baker et al., Mutation Res., 208, 87 (1988)
(17) G. Klein et al., Biochemistry, 27, 1897 (1988)
(18) E. Castro et al., Br. J. Pharmacol., 100, 360 (1990)
(19) D. R. Elmaleh et al., Proc. Natl. Acad. Sci., 81, 918 (1984)
(20) R. Bone et al., J. Biol. Chem., 261, 16410 (1986)
(21) Fed. Amer. Soc. Exper. Bio., Abstr. Part I, no. 1878 (1991)
(22) M. T. Miras-Portugal et al., Ann. NY Acad. Sci., 603, 523 (1990)
(23) A. Guranowski et al., Biochemistry, 27, 2959 (1988)
(24) F. Grummt et al., Plant Mol. Bio., 2, 41 (1983)
(25) A. G. McLennan et al., Nucleic Acid Res., 12, 1609 (1984)
(26) P. Zamecnik et al., Analytical Biochem., 134, 1 (1983)
(27) E. Rapaport et al., Proc. Natl. Acad. Sci., 78, 838 (1981)
(28) T. Kimura et al., Biol. Pharm. Bull., 18, 1556 (1995)
(29) E. Schulze-Lohoff et al., Hypertension, 26, 899 (1995)
(30) B. K. Kim et al., Proc. Natl. Acad. Sci., 89, 11056 (1992)
(31) P. C. Zamecnik et al., Proc. Natl. Acad. Sci., 89, 2370 (1992)
(32) H. Morii et al., Eur. J. Biochem., 205, 979 (1992)
(33) E. Castro et al., Pflugers Arch., 426, 524 (1994)
(34) H. Schluter et al., Nature, 367, 186 (1994)
(35) E. Castro et al., Br. J. Pharmacol., 206, 833 (1992)
(36) T. Casillas et al., Biochemistry, 32, 14203 (1993)
(37) J. Pintor et al., J. Neurochem., 64, 670 (1995)
(38) E. Castro et al., J. Biol. Chem., 270, 5098 (1995)
(39) V. A. Panchenko et al., Neuroscience, 70, 353 (1996)
(40) E. Castro et al., Br. J. Pharmacol., 100, 360 (1990)

(41) J. Pintor et al., Gen. Pharmac., 26, 229 (1995)
(42) J. Pintor et al., Br. J. Phamacol., 115, 895 (1995)
(43) A. Kanavarioti et al., Tett. Lett., 32, 6065 (1991)

SUMMARY OF THE INVENTION

The invention provides novel compounds of Formula I and pharmaceutical compositions thereof. The invention also provides compounds useful in the clearance of retained mucous secretion and the enhancement of ciliary beat frequency. Accordingly, a broad embodiment of the invention is directed to compounds of general Formula I or the pharmaceutically acceptable esters or salts thereof:

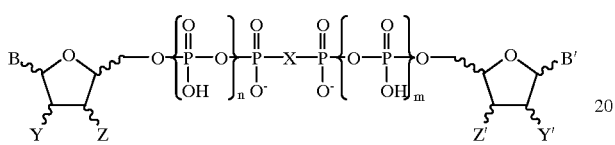

Formula I wherein:

X is oxygen, methylene, difluoromethylene, imido;

n=0, 1 or 2;

m=0, 1 or 2;

n+m=0,1, 2, 3 or 4; and

B and B' are each independently a purine residue or a pyrimidine residue linked through the 9- or 1-position, respectively;

Z=OH or $N_3$;

Z'=OH or $N_3$;

Y=H or OH;

Y'=H or OH; provided that when Z is $N_3$, Y is N, or when Z' is $N_3$, Y' is H; and further provided that the compounds of Table I are excluded.

The compounds of the present invention are highly selective agonists of the $P2Y_2$ and/or $P2Y_4$ purinergic receptor; thus, they may be useful in the treatment of chronic obstructive pulmonary diseases such as chronic bronchitis, PCD, and cystic fibrosis, and may also be useful in the treatment of immobilized patients who are at risk for developing pneumonia. Furthermore, because of their general ability to clear retained mucus secretions and stimulate ciliary beat frequency, the compounds of the present invention may also be useful in the treatment of sinusitis, otitis media and nasolacrimal duct obstruction. They may also be useful for the treatment of dry eye, retinal detachment and wound healing. In addition, because of the pharmacological actions of these compounds, they are useful in facilitating sputum induction procedures. Additionally, it is postulated that the compounds of the present inventions could enhance the performance of athletes by increasing the clearance of mucous secretions from the lungs.

DETAILED DESCRIPTION OF THE INVENTION

This invention provides novel compounds of Formula I and pharmaceutical compositions thereof. The invention also provides compounds useful in the clearance of retained mucous secretion and the enhancement of ciliary beat frequency. Accordingly, a broad embodiment of the invention is directed to novel compounds of general Formula I:

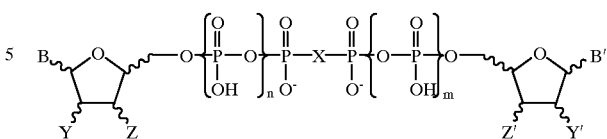

Formula I wherein:

X is oxygen, methylene, difluoromethylene, imido;

n=0, 1 or 2;

m=0, 1 or 2;

n+m=0,1, 2, 3 or 4; and

B and B' are each independently a purine residue or a pyrimidine residue linked through the 9- or 1-position, respectively;

Z=OH or $N_3$;

Z'=OH or $N_3$;

Y=H or OH;

Y'=H or OH;

provided that when Z is $N_3$, Y is H or when Z' is $N_3$, Y' is H; and further provided that the compounds of Table I are excluded; or pharmaceutically acceptable esters or salts thereof.

The furanose sugar is preferably in the β-configuration.

The furanose sugar is most preferably in the β-D-configuration.

Preferred compounds of Formula I are the compounds of Formula IA

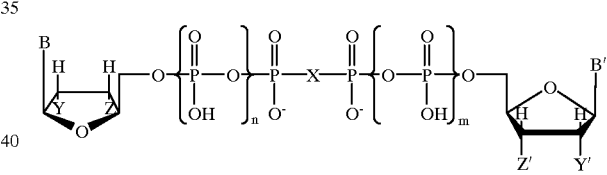

Formula IA wherein:

X=O;

n+m=1 or 2;

Z, Z', Y and Y'=OH;

B and B' are uracil, thymine, cytosine, guanine, adenine, xanthine, hypoxanthine or as defined in Formulas II and III; or

X=O;

n+m=3 or 4;

Z, Z', Y and Y'=OH;

B=uracil;

B' is uracil, thymine, cytosine, guanine, adenine, xanthine, hypoxanthine or as defined in Formulas II and I; or

X=O;

n+m=1 or 2;

Z, Y and Z'=OH;

Y'=H;

B=uracil;

B' is uracil, thymine, cytosine, guanine, adenine, xanthine, hypoxanthine or as defined in Formulas HI and III; or X=O;
n+m=0, 1 or 2;
Z and Y=OH;
Z'=N$_3$;
Y'=H;
B=uracil;
B'=thymine; or X=O;
n+m=0, 1 or 2;
Z and Z'=N$_3$;
Y and Y'=H;
B and B'=thymine; or X=CH$_2$, CF$_2$ or NH;
n and m=1;
Z, Z', Y and Y'=OH;
B and B' are is uracil, thymine, cytosine, guanine, adenine, xanthine, hypoxanthine or as defined in Formulas II and III;

provided that the compounds of Table I are excluded; or pharmaceutically acceptable salts thereof.

Another preferred group of the compounds of Formula I are the compounds of Formula IB or the pharmaceutically acceptable salts thereof:

Formula IB

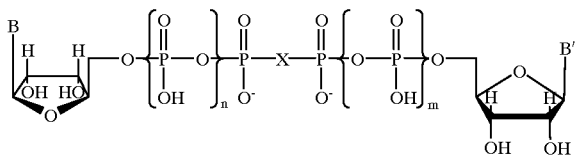

wherein:

X is oxygen, methylene, difluoromethylene or imido;
n=0 or 1;
m=0 or 1;
n+m=0, 1 or 2; and
B and B' are each independently a purine residue, as in Formula II, or a pyrimidine residue, as in Formula III, linked through the 9- or 1-position, respectively. In the instance where B and B' are uracil, attached at N-1 position to the ribosyl moiety, then the total of m+n may equal 3 or 4 when X is oxygen (see example 5). The ribosyl moieties are in the D- configuration, as shown, but may be L-, or D- and L-. The D- configuration is preferred.

Formula II

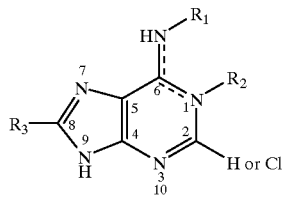

wherein:

R$_1$ is a hydrogen, an alkyl or aryl moiety as defined below or ω-A(C$_{1-6}$alkyl)CONH(C$_{1-6}$alkyl)-wherein A is amino, mercapto, hydroxy or carboxyl;

R$_2$ is O (adenine 1-oxide derivatives), or is absent (adenine derivatives); or R$_1$ and R$_2$ taken together form a 5-membered fused imidazole ring (1, N$^6$-ethenoadenine derivatives), optionally substituted on the 4- or 5-positions of the etheno moiety with alkyl, aryl or aralkyl moieties as defined below;

R$_3$ is alkyl, aryl or aralkyl, alkylamino, arylamino or aralkylamino (NHR'); alkoxy, aryloxy or aralkyloxy (OR'); alkylthio, arylthio or aralkylthio (SR') as defined below; or ω-A(C$_{1-6}$alkyl)CONH(C$_{1-6}$alkyl)B- wherein A and B are independently amino, mercapto, hydroxy or carboxyl; or pharmaceutically acceptable esters, amides or salts thereof.

Thus the substituted derivatives of adenine include adenine 1-oxide; 1,N$^6$-(4- or 5-substituted etheno) adenine; 6-substituted adenine; or 8-substituted aminoadenine, where R' of wherein the 6- or 8-HNR' groups are chosen from among: arylalkyl (C$_{1-6}$) groups with the aryl moiety optionally functionalized as described below; alkyl; and alkyl groups with functional groups therein, such as: ([6-aminohexyl]carbamoylmethyl)-, and ω-acylated-amino (hydroxy, thiol and carboxy)alkyl(C$_{2-10}$)- and their ω-acylated-amino (hydroxy, thiol and carboxy) derivatives where the acyl group is chosen from among, but not limited to, acetyl, trifluoroacetyl, benzoyl, substituted-benzoyl, etc., or the carboxylic moiety is present as its ester or amide derivative, for example, the ethyl or methyl ester or its methyl, ethyl or benzamido derivative. The ω-amino (hydroxy, thiol) moiety may be alkylated with a C$_{1-4}$ alkyl group.

Likewise, B or B', or both, may be a pyrimidine with the general formula of Figure III, linked through the 1- position:

Formula III

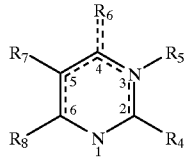

wherein:

R$_4$ is hydrogen, hydroxy, mercapto, amino, cyano, aralkoxy, C$_{1-6}$ alkylthio, C$_{1-6}$ alkoxy, C$_{1-6}$ alkylamino or dialkylamino, the alkyl groups optionally linked to form a heterocycle;

R$_5$ is hydrogen, acyl (e.g., acetyl or benzoyl), C$_{1-6}$ alkyl, aroyl, optionally functionalized as defined below, C$_{1-5}$ alkanoyl, benzoyl, or sulphonate;

R$_6$ is hydroxy, mercapto, alkoxy, aralkoxy, C$_{1-6}$alkylthio, amino, C$_{1-5}$ disubstituted amino, triazolyl, alkylamino or dialkylamino, where the alkyl groups are optionally linked to form a heterocycle or link to $N^3$ to form an optionally substituted ring; or $R_5$ and $R_6$ taken together form a 5-membered fused imidazole ring between positions 3 and 4 of the pyrimidine ring (3,$N^4$-ethenocytosine derivatives) optionally substituted on the 4- or 5- positions of the etheno moiety with alkyl, aryl or aralkyl moieties as defined below.

$R_7$ is hydrogen, hydroxy, cyano, nitro, alkenyl with the alkenyl moiety optionally linked through oxygen to form a ring optionally substituted on the carbon adjacent to the oxygen with alkyl or aryl groups, substituted alkynyl, halogen, substituted alkyl, perhalomethyl (e.g., $CF_3$), $C_{2-6}$ alkyl, $C_{2-3}$ alkenyl, or substituted ethenyl (e.g., allylamino, bromovinyl and ethyl propenoate, or propenoic acid), $C_{2-3}$ alkynyl or substituted alkynyl; or together $R_6$–$R_7$ may form a 5 or 6-membered saturated or unsaturated ring bonded through N or O at $R_6$, such a ring may contain substituents that themselves contain functionalities; provided that when $R_8$ is amino or substituted amino, $R_7$ is hydrogen; and $R_8$ is hydrogen, amino or substituted amino, alkoxy, arylalkoxy, alkylthio, arylalkylthio, carboxamidomethyl, carboxymethyl, methoxy, methylthio, phenoxy or phenylthio; or pharmaceutically acceptable esters, amides or salts thereof.

In the general structures of Formula II and III above, the acyl groups advantageously comprise alkanoyl or aroyl groups. The alkyl groups which may be straight or branched advantageously contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups advantageously contain 2 to 8 carbon atoms, particulary 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are advantageously selected from halogen, hydroxy, $C_{1-4}$ alkoxy, $C_{1-4}$ alkyl, $C_{6-10}$ aryl, $C_{7-12}$ arylalkyl, $C_{7-12}$ arylalkoxy, carboxy, cyano, nitro, sulfonamido, sulfonate, phosphate, sulfonic acid, amino and substituted amino wherein the amino is singly or doubly substituted by a $C_{1-4}$ alkyl, and when doubly substituted, the alkyl groups optionally being linked to form a heterocycle.

The compounds of the present invention encompass their pharmaceutically acceptable esters, such as, but not limited to, acetyl and benzoyl esters. The esters may be made by reaction of the desired hydroxy compound with the appropriate acid, activated with carbonyldiimidazole, dicyclohexylcarbodiimide or other suitable condensing agent, or with an acid anhydride or acid chloride with or without a basic catalyst such as a tertary amine, quaternary amonium salt or an inorganic base.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects. The present invention also encompasses the acylated prodrugs (e.g., esters) of the compounds disclosed herein. Those skilled in the art will recognize various synthetic methodologies which may be employed to prepare non-toxic pharmaceutically acceptable salts and acylated prodrugs of the compounds encompassed by Formulas I, IA and IB.

The compounds of the present invention are highly selective agonists of the $P2Y_2$ and/or $P2Y_4$ purinergic receptor; thus, they are useful in the treatment of mammals including humans suffering from chronic obstructive pulmonary diseases such as chronic bronchitis, PCD, cystic fibrosis, as well as prevention of pneumonia due to immobility. Furthermore, because of their general ability to clear retained mucus secretions and stimulate ciliary beat frequency, the compounds of the present invention are also useful in the treatment of sinusitis, otitis media and nasolacrimal duct obstruction in mammals, including humans. Additionally, the compounds of the present invention are useful for treating mammals including humans with dry eye and retinal detachment.

Though the compounds of the present invention are primarily concerned with the treatment of human subjects, they may also be employed for the treatment of other mammalian subjects such as dogs and cats for veterinary purposes.

The pharmaceutical utility of compounds of this invention are indicated by the inositol phosphate assay for $P2Y_2$ and other P2Y receptor activity. This widely used assay, as described in E. Lazarowski, et al., *Brit. J. Pharm.* 116, 1619–27 (1995), relies on the measurement of inositol phosphate formation as a measurement of activity of compounds activating receptors linked via G-proteins to phospholipase C.

The compounds of general Formulas I, IA, or IB may be administered orally, topically, parenterally, by inhalation or spray, intra-operatively, rectally, or vaginally in dosage unit formulations containing conventional non-toxic pharmaceutically acceptable carriers, adjuvants and vehicles. The term topically as used herein includes patches, gels, creams, ointments, or nose, ear or eye drops. The term parenteral as used herein includes subcutaneous injections, intravenous, intramuscular, intrasternal injection or infusion techniques. In addition, there is provided a pharmaceutical formulation comprising a compound of general Formulas I, IA or IB and a pharmaceutically acceptable carrier. One or more compounds of general Formulas I, IA or IB may be present in association with one or more non-toxic pharmaceutically acceptable carriers or diluents or adjuvants and, if desired, other active ingredients. One such carrier would be sugars, where the compounds may be intimately incorporated in the matrix through glassification or simply admixed with the carrier (e.g., lactose, sucrose, trehalose, mannitol) or other acceptable excipients for lung or airway delivery.

One or more compounds of general Formulas I, IA or IB may be administered separately or together, or separately or together with mucolytics such as DNAse or acetylcysteine.

The pharmaceutical compositions containing compounds of general Formulas I, IA or IB may be in a form suitable for oral use, for example, as tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the active materials in admixture with excipients suitable for the manufacture of aqueous suspensions. Such excipients are suspending agents, for example: sodium carboxymethylcellulose, methylcellulose and sodium alginate. Dispersing or wetting agents may be a naturally-occurring phosphatide or condensation products of an allylene oxide with fatty acids, or condensation products of ethylene oxide with long chain aliphatic alcohols, or condensation products of ethylene oxide with partial esters from fatty acids and a hexitol, or condensation products of ethylene oxide with partial esters derived from fatty acids and hexitol anydrides. Those skilled in the art will recognize the many specific excipients and wetting agents encompassed by the general description above. The aqueous suspensions may also contain one or more preservatives, for example, ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Compounds of general Formulas I, IA or IB may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle. The sterile injectable preparation may be a sterile injectable solution or suspension in a non-toxic parentally acceptable diluent or solvent. Among the acceptable vehicles and solvents that may be employed are sterile water, saline solution, or Ringer's solution.

The compounds of general Formulas I, IA or IB may also be administered in the form of suppositories for ear, rectal or vaginal administration of the drug. These compositions can be prepared by mixing the drug with a suitable non-irritating excipient which is solid at ordinary temperatures but liquid at the body temperature and will therefore melt to release the drug. Such materials are cocoa butter and polyethylene glycols.

Solutions of compounds of general Formulas I, IA or IB may be administered by intra-operative installation.

Dosage levels of the order of from about $10^{-7}$ M to about $10^{-1}$ M, preferably in the range $10^{-5}$ to $10^{-1}$M, are useful in the treatment of the above-indicated conditions. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Compounds encompassed by the present invention may be prepared by condensation of a nucleoside mono-, di-, or triphosphate, activated with a condensing agent such as, but not limited to, carbonyldiimidazole or dicyclohexylcarbodiimide, with a second molecule of the same or a different mono-, di-, or triphosphate to form the desired dinucleotide polyphosphate; or a nucleoside phosphate, activated as above, may be condensed sequentially with a non-nucleoside mono-, di- or polyphosphate moiety, such as, but not limited to a monophosphate or pyrophosphate anion to yield the desired dinucleotide polyphosphate, the non-isolated intermediate in such a case being a mononucleotide polyphosphate; or a mono-, di- or polyphosphate moiety, activated as mentioned above, or in the form of an acid halide or other derivative reactive toward nucleophilic displacement, may be condensed sequentially with a nucleoside phosphate or polyphosphate to yield the desired dinucleotide polyphosphate; or the desired dinucleotide polyphosphate may be formed by modification a pre-formed dinucleotide polyphosphate by substitution or derivatization of a moiety or moieties on the purine, pyrimidine or carbohydrate ring. Nucleoside phosphates used as starting materials may be commercially available, or may be made from the corresponding nucleosides by methods well known to those skilled in the art. Likewise, where nucleosides are not commercially available, they may be made by modification of other readily available nucleosides, or by synthesis from heterocyclic and carbohydrate precursors by methods well known to those skilled in the art.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

Preparation of $P^1,P^4$-Di(uridine 5'-)$P^2,P^3$-methylenetetraphosphate

Methylenediphosphonic acid (Aldrich, 0.0088 g, 0.05 mmol) was dissolved in anhydrous DMF (0.5 mL) with the addition of tributylamine (24 μL, 0.1 mmol). The solution was evaporated to dryness twice with anhydrous DMF (2×1 mL), the dried residue dissolved in anhydrous DMF (0.5 mL), and a solution of similarly-dried uridine 5'-monophosphomorpholidate 4-morpholine-N,N'-dicyclohexylcarboxamidine salt (Sigma, 0.137 g, 0.2 mmol) in anhydrous DMF (0.5 mL) added. The reaction mixture was heated at 80–90° C. for 7 h; then the solvent was removed by evaporation under reduced pressure. The residue was dissolved in water (2 mL) and applied to a column of DEAE cellulose (2.5×50 cm bed volume) in the bicarbonate form. The column was eluted with water, followed by a gradient of ammonium bicarbonate (0–0.33 M, in 900 mL). The progress of the elution was followed by monitoring absorbance of the eluate at 254 nm; the fraction eluting between 0.23 and 0.26 M was collected, evaporated to dryness and desalted by repeated evaporation with deionized water. The residue was dissolved in water (300 μL) and purified in 50 μL aliquots by semipreparative HPLC (Alltech PEI 5μ, 10×250 mm, gradient 0–0.66-M ammonium bicarbonate, 5.0 mL/min, 20 min); peaks eluting at 8.7–9.0 min from each run were combined and lyophilized to yield the title compound (0.007 mmol, 14% yield, quantitated by comparison of its absorbance at $\lambda_{max}$ 263 with that of a standard solution of uridine monophosphate). Chromatographic purity was 96.5% on an Alltech PEI column, gradient 0–0.66-M ammonium bicarbonate, 1.0 mL/min, 20 min., retention time 13.03 min. $^1$H NMR in $D_2O$ (δ ppm from tetramethylsilane): 2.39, (t, J=21.5 Hz, 2H); 4.12 (m, 6H); 4.243 (m, 4H); 5.841 (d, J=7.9 Hz, 2H); 5.847 (d, J=4.5 Hz, 2H); 7.77, d, J=8.1 Hz, 2H). $^{31}$P NMR in $D_2O$ (ppm from $H_3PO_4$)–10.2 to –10.7 (complex m, 2P); 7.8 to 8.4 (complex m, 2P).

EXAMPLE 2
Preparation of $P^1,P^4$-Di(uridine 5'-$P^2,P'$-difluoromethylenetetraphosphate)

The tributylammonium salt of difluoromethylenediphosphonic acid (as described in C. McKenna, et al., *J. Org. Chem.* 46,4574–76 (1981) and D. Burton, et al., *J. Fluorine Chem.* 15, 263–66 (1980)) (0.014 g, 0.025 mmol), converted to the salt as described for methylenephosphonic acid was dissolved in a solution of uridine 5'-monophosphomorpholidate 4-morpholine-N,N'-dicyclohexylcarboxamidine salt (Sigma, 0.034 g, 0.05 mmol) in anhydrous dimethyl sulfoxide (0.7 mL), and heated for 9 days at 50° C. The cooled reaction mixture was diluted with water and applied to a column of DEAE cellulose (2.5×50 cm bed volume) in the bicarbonate form. The column was eluted with water, followed by a gradient of ammonium bicarbonate (0–0.33 M, total volume 900 mL). The progress of the elution was followed by monitoring absorbance of the eluate at 254 nm. The fraction eluting between 0.29 and 0.30 M was evaporated to dryness and desalted by repeated evaporations with deionized water to yield the title compound (0.0011 mmol, 4.4% yield, quantitated by comparison of its absorbance at $\lambda_{max}$ 263 nm with that of a standard solution of uridine monophosphate). Chromatographic purity was 88.5% on an Alltech PEI column, gradient 0–0.66-M ammonium bicarbonate, 1.0 mL/min., 20 min, retention time 12.03 min. $^1$H NMR in $D_2O$ (δ ppm from tetramethylsilane): 4.05–4.085 (m, 6H); 4.18–4.20 (m, 4H); 5.80 (d, J=8.0 Hz, 2H); 5.81 (d, J=4.5 Hz, 2H); 7.77 (d, J=7.9 Hz, 2H). $^{31}$P NMR in $D_2O$ (δ ppm from $H_3PO_4$)–10.63 (dd, J=18.3, 11.3 Hz, 2P);–5.83 (tdd, J=75, 18.3, 11.3 Hz, 2P). $^{19}$F NMR in $D_2O$: 73.406 (t, J=75.5 Hz).

EXAMPLE 3
Preparation of $P^1,P^4$-Di(uridine 5'-$P^2,P^3$-imidotetraphosphate)

Tetrasodium imidodiphosphate (Sigma, 0.05 mmol) was dissolved in water 0.5 mL) and applied to a column of Biorad AG-MP50 strong cation exchange resin (2 mL bed volume, 3 meq) in its tributylamine form. The column was eluted with water (~10 mL), the eluate lyophilized dried by evaporation with dry DMF. Treatment of uridine 5'-monophosphomorpholidate 4-morpholine-N,N'-dicyclohexylcarboxamidine salt (Sigma, 0.068 g, 0.1 mmol) with a solution of the tetrabutylammonium imidodiphosphate (0.05 mmol) in anhydrous DMF (1.0 mL) for 20 days at room temperature, and isolation essentially as described above yielded the title compound as the ammonium salt (1.6%). $^1$H NMR in $D_2O$ (δ ppm from tetramethylsilane): 4.07–4.09 (m, 6H); 4.17–4.22 (m, 4H); 5.79 (d, J=8.1 Hz, 2H); 5.80 (d, J=4.8 Hz, 2H); 7.78, d, J=8.2 Hz, 2H). $^{31}$P NMR in $D_2O$ (δ ppm from $H_3PO_4$)–10.82 (m, 4P); P-P coupling pattern similar to that of $P^1,P^4$-di(adenosine 5'-tetraphosphate (Sigma) run under same conditions.

EXAMPLE 4
Preparation of $P^1,P^4$-Di(4-thiouridine 5'-tetraphosphate)

4-Thiouridine monophosphate sodium salt (Sigma, 25 mg, 0.057 mmol) was dissolved in water 0.5 mL), applied to a column of Biorad AG-MP50 strong cation exchange resin (2 mL bed volume, 3 meq) in its tributylamine form, the column eluted with water (~10 mL) and the eluate lyophilized. The tributylammonium salt was dissolved in anhydrous DMF (0.5 mL) and carbonyldiimidazole (4.86 mg, 0.03 mmol) was added. The reaction mixture was set aside under nitrogen at room temperature for twelve days. The reaction mixture was evaporated to dryness under vacuum at room temperature, the residue dissolved in water (2 mL), and applied to a column of DEAE cellulose (2.5×50 cm bed volume) in the bicarbonate form. The column was eluted with water (~250 mL), then with a gradient of ammonium bicarbonate (0–0.33 M, total volume 900 mL). This was followed by a gradient of 0.33 to 0.5 M ammonium bicarbonate over 400 mL. The progress of the elution was followed by monitoring absorbance of eluate at 280 nm. The fraction eluting between 0.336 and 0.339 M was evaporated to dryness and desalted by repeated evaporations with deionized water to yield the title compound (0.0045 mmol, 18% yield, quantitated by comparison of its absorbance at $\lambda_{max}$ 332 nm with that of a standard solution of 4-thiouridine diphosphate). $^1$H NMR in $D_2O$ (δ ppm from tetramethylsilane): 4.09–4.11 (m, 6H); 4.18–4.24(m, 4H); 5.76 (d, J=4.5 Hz, 2H); 6.47 (d, J=7.7 Hz, 2H); 7.67, d, J=8.2 Hz, 2H). $^{31}$P NMR in $D_2O$ (δ ppm from $H_3PO_4$)–22.57 to –22.73 (m, 2P); –10.76 to –10.91 (m, 2P); P-P coupling pattern similar to that of $P^1,P^4$-di(adenosine 5'-tetraphosphate (Sigma) run under same conditions.

Example 5
Preparation of $P^1,P^5$-Di(uridine 5'-pentaphosphate) p A 100 ml round bottomed flask was charged with a DMF solution of uridine 5'-diphosphate tributylammonium salt (1.81 mmol, 10 ml) and carbonyldiimidazole (469 mg, 2.90 mmol) and the solution was stirred under $N_2$ for 2 hours. To this was added a DMF solution of uridine 5'-triphosphate tributylammonium salt (1.81 mmol, 10 ml) and the solution was stirred at 60° C. for 24 hours. The solution was evaporated in vacuo and purified two times by column chromatography (DEAE Sephadex; $H_2O$>0.5 M $NH_4HCO_3$ gradient). The pure fractions were concentrated in vacuo at 35° C., and $H_2O$ added and reevaporated ten times to obtain a white solid (200 mg). $^1$H NMR in $D_2O$ (δ ppm from tetramethylsilane): 4.0 (m, br, 6H), 4.1 (m, 4H), 5.7 (m, 4H), 7.7 (d, J=8.1 Hz, 2H); $^{31}$P NMR in $D_2O$ (δ ppm from $H_3PO_4$)–22.3 (m, 3P),–10.6 (d, J=42.9 Hz, 2P).

EXAMPLE 6

Preparation of $P^1,P^4$-Di(3,$N^4$-ethenocytidine 5'-)tetraphosphate

To a solution of $P^1,P^{4-}$di(cytidine 5'-)tetraphosphate (reference 3, Table I; ammonium salt, 6 μmol in 0.66 mL water) was added sodium bicarbonate (0.005 g, 60 μmol) and the solution was lyophilized to remove ammonia. The residue was dissolved in a mixture of water and (0.20 mL) and chloroacetaldehyde solution (50% in water, 0.30 mL), and the reaction mixture set aside at room temperature for six days. The reaction mixture was lyophilized, and the gummy residue partitioned between deuterium oxide (0.7 mL) and methylene chloride (1.5 mL). The $^1$H NMR spectrum of the aqueous solution indicated that the ethenylation had progressed about 50%, while the $^{31}$P spectrum confirmed that the tetraphosphate chain remained intact. Additional chloroacetaldehyde solution (0.25 mL) was added to the NMR solution and the mixture set aside for a further ten days. The solution was lyophilized, and the residue lyophilized again with deuterium oxide to remove exchangeable protons. The residue was partitioned between deuterium oxide and methylene chloride as before, and complete conversion to the ethenyl derivative confirmed by NMR spectroscopy. The deuterium oxide solution was applied to a column of DEAE cellulose (2.5×30 cm bed volume) in the bicarbonate form. The column was eluted with water (~250 mL), followed by a gradient of 0 to 0.5 M ammonium bicarbonate over 1000 mL. The progress of the elution was followed by monitoring absorbance of the eluate at 280 nm. The fraction eluting between 0.29 and 0.32 M was evaporated to dryness and desalted by repeated evaporations with deionized water to yield the title compound (1.584 μmol, 26.4% yield, quantitated by comparison of its absorbance at $\lambda_{max}$ 273 nm with that of a standard solution of 3,$N^4$-ethenocytidine 5'-monophosphate). $^1$H NMR in $D_2O$ (δ ppm from tetramethylsilane): 4.123 (m, 6H); 4.258 (m, 4H); 5.986 (s, 2H); 6.92 (d, J=8.1 Hz, 2H); 7.461 (s, 2H); 7.772 (s, 2H); 8.00 (d, J=7.6 Hz, 2H). $^{31}$P NMR in $D_2O$ (δ ppm from $H_3PO_4$)−22.474 (m, 2P);−10.650 (m, 2P); P-P coupling pattern closely similar to that of $P^1,P^4$-di(adenosine 5'-tetraphosphate [Sigmna]) run under same conditions.

EXAMPLE 6(a)

$P^1$, $P^4$-Di(imidazo[1,2-c]pyrimidin-5(6H)-one-2-(3-nitro)-phenyl-6-β-D-ribofuranoside 5'-)tetraphosphate, Tetraammonium Salt $P^1,P^4$-Di(cytidine 5'-)tetraphosphate, tetraammonium salt (100 mg, 0.117 mmol) (reference 3, Table I) was dissolved in water (10 mL) and flushed through a column of Dowex 50H$^+$ resin (3 g, pre-washed with methanol and water) and washed with 50 mL water. Tributylamine (1 mL) and dimethylformamide (DMF) (5 mL) were added and the solution was evaporated to an oil. The oil was dissolved in dry DMF (10 mL) and the evaporation cycle repeated twice. The final oil was dissolved in dry DMF (10 mL) and tributylamine (1.5 mL) to which was added α-bromo-3'-nitro-acetophenone (86 mg, 0.351 mmol). The reaction mixture was heated under nitrogen gas at 70° C. for 20 hr, when more α-bromo-3'-nitro-acetophenone (50 mg, 0.205 mmol) was added. After heating for an additional 18 hr, the solvent was removed in vacuo and the residue purified by flash chromatography (DEAE Sephadex, 0>1.0 M $NH_4HCO_3$) to obtain a yellow solid (13.5 mg): $^1$H NMR ($D_2O$, TMS) δ4.0–4.2 (m, br, 10H), 6.0 (d, J=5.7 Hz, 2H), 6.4 (d, J=8.1 Hz, 2H), 7.35 (t, J=7.8 Hz, 2H), 7.5 (d, J=8.1 Hz, 2H), 7.80 (m, 3H), 8.03 (s, 2H); $^{31}$P NMR ($D_2O$, $H_3PO_4$ std)δ−10.67 (m, 2P), −22.26 (m, 2P).

EXAMPLE 7

$P^1$-(Thymidine-5'-)$P^4$-(uridine-5'-)tetraphosphate ($UP_4T$)

A solution of uridine 5'-triphosphate (UTP) trisodium salt (ProBioSint, 5.86 g, 0.01 mol) in water (5 mL) was passed through a column of BioRad AG-MP 50 strong cation exchange resin in its tributylamine form (50 mL bed volume) and eluted with distilled water (about 300 mL). To this solution was added tributylamine (5 mL), and the suspension shaken until the pH of the aqueous fraction had risen to 8. The layers were separated and the aqueous solution evaporated to small volume, then lyophilized overnight. The residue was dissolved in dry dimethylformamide (DMF, 20 mL) and the solvent evaporated at 0.1 mmHg. The dried tributylamine salt was made up to 100 mL with anhydrous acetone to yield a stock solution (0.1 M in UTP). Dicyclohexylcarbodiimide(DCC) (baker, 0.1 g, 0.5 mmol) was added to an aliquot of the foregoing UTP solution (1.0 mL 0.1 mmol) and the solution stirred at room temperature for 30 min. The deposited dicyclohexylurea was removed by filtration, the reaction mixture extracted with ether (10 mL), and the residue dissolved in dry deuterated dimethylsulfoxide (DMSO-$d_6$, 0.3 mL). This solution of uridine 5'-cyclic metaphosphate (UcTP) was added to a solution of thymidine 5'-monophosphate (TMP, 0.064 g, 0.2 mmol) and tributylamine (0.2 mL) in DMSO-$d_6$ (0.3 mL) and set aside at 50° C. for 24 h. The reaction mixture was evaporated under high vacuum overnight, the residue dissolved in water (1.0 mL), filtered to remove a little residual dicyclohexylurea, and separated by semipreparative ion-exchange chromatography (Hamilton PRP X-100 column, eluting with isocratic 1.0 M ammonium bicarbonate, 5 mL/min, 30 min, multiple injections of 100 μL). The dinucleotide tetraphosphate eluted between 21 and 23 min; the product (11.1 % yield based on UTP) was quantitated by comparison of its ultraviolet absorption at $\lambda_{max}$263 nm with those of standards of UMP and TMP. $^1$H NMR $D_2O$, δ ppm from tetramethylsilane: 1.78 (s, 3H); 2.19–2.22 (m, 2H); 4.04–4.13 (m, 6H) 4.22–4.27 (m, 2H); 4.52 (m, partially obscured by D2O); 4.74 (m, partially obscured by D2O); 5.83 (d, J=8.1 Hz, 1H); 5.84 (d, J=5.0 Hz, 1H); 6.195 (t, J=6.9 Hz, 1H); 7.61 (s, 1H); 7.82 (d, J=8.1 Hz, 1H). $^{31}$P NMR ($D_2O$, δ ppm from $H_3PO_4$)−22.71 (m, 2P);−10.97 (m, 2P).

EXAMPLE 8

$P^1$-(Inosine 5'-)$P^4$-(uridine 5'-)tetraphosphate ($UP_4I$)

Condensation of uridine 5'-cyclic trimetaphosphate (UcTP) and inosine 5'-monophosphate was carried out essentially as described above, except that the reaction mixture was stored at 25° C. for five weeks prior to evaporation of the solvent. The residue was dissolved in water (1.0 mL), filtered, and separated in 150 μL aliquots by ion exchange chromatography on a Hamilton PRP X-100 column, eluting with isocratic 1.0 M ammonium bicarbonate, 5 mL/min, 30 min. The fractions eluting between 6 and 9 minutes were evaporated and lyophilized overnight to remove buffer. The dinucleotide tetraphosphate (8% yield, 96% purity by HPLC (AUC)) was quantitated by comparison of its ultraviolet absorption at 260 nm with those of UMP and IMP at the same wavelength. $^1$H NMR ($D_2O$, δ ppm from tetramethylsilane): 4.13 (m, 6H) 4.24–4.27 (m, 2H); 4.47 (m, partially obscured by D2O); 5.78 (d, J=7.9 Hz, 1H); 5.83 (d, J=4.7 Hz, 1H); 6.003 (d, J=5.7 Hz, 1H); 7.79 (d, J=7.9 Hz, 1H); 8.10 (s, 1H); 8.37 (s, 1H). $^{31}$P NMR ($D_2O$, δ ppm from $H_3PO_4$)−22.43 (m, 2P); −10.72 (m, 2P).

EXAMPLE 9

$P^1$-(4-Thiouridine 5'-)$P^4$-(uridine 5'-)tetraphosphate ($UP_4$ (4-SH-U))

4-Thiouridine monophosphate sodium salt (25 mg, 0.057 mmol) was dissolved in water (0.5 mL), applied to a column of Biorad AG-MP50 strong cation exchange resin (2 mL bed volume, 3 meq) in its tributylamine form, the column eluted with water (~10 mL) and the eluate lyophilized. The resulting tributylamine salt of 4-thio-UNP was condensed with uridine 5'-cyclic trimetaphosphate (0.1 mmol) prepared by activation of UTP with dicyclohexylcarbodiimide (206 mg) essentially as described in Example 7 (72 h reaction time). After evaporation of the DMSO from the reaction mixture, the residue was dissolved in water (~1 mL) and and separated in 200 µL aliquots by ion exchange chromatography on a Hamilton PRP X-100 column, eluting with isocratic 1.0 M ammonium bicarbonate, 5 mL/min, monitoring the elution at 328 nm. The fractions eluting between 15 and 25 min were lyophilized to give the title compound (9.7% yield, 99.7% pure by HPLC(AUC)), which was quantitated by comparison of its ultraviolet absorption at 332 nm with that of 4-thio-UMP at the same wavelength. $^1$H NMR ($D_2O$, δ ppm from tetramethylsilane): 4.04 (m, partially overlapped by HOD); 4.14 (m, partially overlapped by HOD); 5.72 (m, 3H); 6.42 (d, J=7.4 Hz); 7.55 (d, J=7.6 Hz); 7.70 (d, J=8.1 Hz). $^{31}$P NMR ($D_2O$, δ ppm from $H_3PO_4$)–20.88 (m, 2P); –9.27 (m, 2P).

Examples 10–12 were prepared from uridine 5'-cyclic trimetaphosphate (0.1 mmol) and the relevant nucleoside 5'-monophosphate (0.2 mmol) essentially as described in Example 7, except that hexane was used in place of ether to extract the excess of DCC from the reaction mixture.

EXAMPLE 10

$P^1$-(Cytosine β-D-arabinofuranoside 5'-)$P^4$-(uridine 5'-) tetraphosphate, ($UP_4araC$) (20 mg)

$^1$H NMR ($D_2O$)δ4.30–3.95 (m,10OH), 5.99 (d,J=6.7 Hz,1H), 6.08 (d,J=5.2 Hz,1H), 7.82–7.77(m,2H); $^{31}$P NMR ($D_2O$) δ–10.79 (m,2P), –22.52 (m,2P)

EXAMPLE 11

$P^1$-(Uridine 5'-)-$P^4$-(xanthosine 5'-)tetraphosphate ($UP_4X$) (27.7 mg)

$^1$H NMR ($D_2O$): δ4.50–4.40 (m,10H), 5.80–5.70 (m,3H), 7.70 (d,J=8.0 Hz,1H), 7.88 (s,1H,); $^{31}$P NMR ($D_2O$): δ–10.73 (m,2P), –22.41 (m,2P)

EXAMPLE 12

$P^1$-(2'-deoxyuridine 5'-)-$P^4$-(uridine 5'-)tetraphosphate ($UP_4dU$) (40.6 mg)

$^1$H NMR ($D_2O$) δ2.20–2.15 (m,2H), 4.45–3.95 (m,9H), 5.80–5.74 (m,3H),6.12 (t,J=6.7 Hz,1H), 7.80–7.74 (m,2H),; $^{31}$P NMR ($D_2O$) δ2.9 (m,2P), –8.9 (m,2P)

EXAMPLE 13

$P^1$-(3'-Azido-3'-deoxythymidine 5'-)-$P^4$-(uridine 5'-) tetraphosphate ($UP_4(AZT)$) and Example 14, $P^1,P^4$-Di(3'-azido-3'-deoxythymidine 5'-)tetraphosphate $(AZT)_2P_4$ 3'-Azido-3'-deoxythymidine 5'-monophosphate (AZTMP) sodium salt (50 mg, 0.135 mmol) was dissolved in water (1 mL) and applied to a column of Biorad AG-MP50 strong cation exchange resin in its tributylamine form. The column was eluted with water (~10 mL) and the eluate lyophilized. The resulting tributylamine salt was condensed with uridine 5'-cyclic trimetaphosphate (0.1 mmol) prepared by activation of UTP with dicyclohexylcarbodiimide (206 mg) essentially as described in Example 7. The residue after evaporation of the reaction mixture was dissolved in water (1.0 mL), passed through a 0.45 µ syringe filter to remove a little solid, and the filtrate subjected to preparative HPLC on a Hamilton PRP X-100 column, eluting with an isocratic mixture of 1.0 M ammonium bicarbonate (75%) and methanol (25%), (4 mL/min). The fraction eluting between 5 and 8 min was lyophilized to yield $UP_4(AZT)$ (7.9%), quantitated by comparison of its ultraviolet absorption at 264 nm with those of UMP and TMP at the same wavelength. $^1$H NMR $D_2O$, δ ppm from tetramethylsilane: 1.78 (s, 3H); 2.30–2.34 (m, 2H); 4.07–4.14 (m, 6H) 4.22–4.29 (m, 2H); 4.52 (m, 1H); 5.82 (d, J=4.4 Hz, 1H); 5.84 (d, J=8.1 Hz, 1H); 6.12 (t, J=7 Hz, 1H); 7.62 (s, 1H); 7.81 (d, J=8.1 Hz, 1H). $^{31}$P NMR ($D_2O$, δ ppm from $H_3PO_4$)–22.51 (m, 2P);–11.06 (m, 1P);–10.81 (m, 1P).

Collection and lyophilization of the fractions eluting between 25 to 40 minutes from the same reaction mixture yielded $P^1,P^4$-Di(3'-azido-3'-deoxythymidine 5'-) tetraphosphate (3%), quantitated by comparison of its ultraviolet spectrum at 266 nm with that of TMP. $^1$H NMR $D_2O$, δ ppm from tetramethylsilane: 1.80 (s, 6H); 2.31–2.35 (m, 4H); 4.09–4.11 (m, 6H) 4.46–4.47 (m, 2H); 6.12 (t, J=7 Hz, 2H); 7.63 (s, 2H). $^{31}$P NMR ($D_2O$, δ ppm from $H_3PO_4$)–22.47 (m, 2P);–11.35 (m, 2P).

EXAMPLE 14

$P^1,P^6$-Di(uridine-5'-)hexaphosphate ($U_2P_6$)

The dinucleotide hexaphosphate (6.97%) was formed by reaction of uridine cyclic trimetaphosphate with uridine 5'-triphosphate under similar conditions. $^1$H NMR $D_2O$, δ ppm from tetramethylsilane: 4.06–4.19 (m, 6H); 4.21–4.4.26 (m, 4H); 5.78 (d, J=8.2 Hz, 2H); 5.81 (d, J=5.4 Hz, 2H); 7.78 (d, J=8.1 Hz, 1H), $^{31}$P NMR ($D_2O$, δ ppm from $H_3PO_4$)–22.41 (m, 4P); –10.89 (m, 2P).

EXAMPLES 15 and 16

2'(3')-Benzoyl-$P^1,P^4$-di(uridine 5'-)tetraphosphate (Example 15) and $P^1,P^4$-Di(2'(3')-benzoyl uridine 5'-)tetraphosphate (Example 16)

Benzoic acid (61.7 mg, 0.505 mmol) and 1,1-carbonyldiimidazole (81.8 mg, 0.505 mmol) were combined in anhydrous DMF (1 mL) and stirred at ambient temperature for 1 hour. $P^1,P^4$-Di(uridine 5'-)tetraphosphate (97 mg, 0.102 mMol) in anhydrous DMF (2 mL) was added and the mixture stirred at ambient temperature for 4 hours. The temperature was increased to 35° C. and stirring continued for 6 days. The reaction mixture was evaporated to dryness, dissolved in water, applied to a Sephadex DEAE A25 column (2.5×20 cm) and eluted with a ammonium bicarbonate gradient (0 to 0.3M, 400 mL total volume) followed by isocratic ammonium bicarbonate (0.5M, 500 mL). Two fractions were collected, evaporated to dryness, then repeatedly co-evaporated with water to remove ammonium salts. The material eluting earlier was identified as the monobenzoyl ester: $^1$H NMR ($D_2O$) δ4.0–4.23 (m,9H), 5.35–5.45 (m,1H), 5.65–5.85 (m,3H), 5.98–6.02 (m, 1H), 7.32–7.95 (m,7H); $^{31}$P NMR ($D_2O$) δ–10.70 (m,2P), –22.28 (m,2P): the material eluting later was identified as the dibenzoyl ester: $^1$H NMR ($D_2O$) δ4.05–4.40 (m,8H), 5.30–6.05 (m,6H), 7.2–7.95 (m,12H); $^{31}$P NMR ($D_2O$) δ–10.70 (m,2P), –22.45 (m,2P)

EXAMPLES 17, 18, 19 and 20

$P^1$-(2'-deoxyguanosine 5'-)$P^4$-(uridine 5'-)tetraphosphate ($UP_4dG$) (Example 17)
$P^1$-(2'-deoxyadenosine 5'-)$P^4$(uridine 5'-)tetraphosphate ($UP_4dA$) (Example 18)
$P^1$-(2'-deoxyinosine 5'-)$P^4$-(uridine 5'-)tetraphosphate ($UP_4dI$) (Example 19) and $P^1$-(2'-deoxycytidine 5'-)$P^4$-(uridine 5'-)tetraphosphate ($UP_4dC$) (Example 20)

Uridine 5'-triphosphate (5.0 g) in water (18 mL) was passed through a column of Dowex 50 H$^+$, and tributylanine (3.0 g) added to the eluent. The mixture was concentrated to an oil, dried by evaporation with dry DMF and redissolved in dry DMF (18 mL). Dicyclohexylcarbodiimide (DCC, 3.5 g) was added, the solution stirred at room temperature for 30 min, and the precipitate removed by filtration. Hexane (70 mL) was added to the filtrate, the bottom layer separated and washed again with hexane (70 mL) to complete the removal of DCC. This solution of uridine 5'-cyclic metaphosphate (UcTP) was used in the following experiments:

EXAMPLE 17

P$^1$-(2'-deoxyguanosine 5'-)P$^4$-(uridine 5'-)tetraphosphate (UP$_4$dG)

2'-Deoxyguanosine 5'-monophosphate (d-GMP, Sigma, 500 mg) was dissolved in DMF (4.5 mL), tributylamine (1.0 mL) added, and the solution concentrated to an oil under vacuum. One third of the solution of uridine 5'-cyclic metaphosphate (UcTP, above) was added and the solution heated at 40° C. for 24 h. The solution was evaporated to an oil, dissolved in water (10 mL) and applied to a column of Sephadex DEAE (350 mL in a 4.5×22 cm column) in its bicarbonate form, pre-equilibrated with 0.25 M ammonium bicarbonate. The column was eluted successively with 0.25, 0.30, 0.35, 0.40, and 0.50 M ammonium bicarbonate. The elution was monitored by HPLC (SynchroPak AX-300, 75% 0.50 M KH$_2$PO$_4$, 25% MeCN 1.0 mL/min, UV 254 nm), and the fraction containing UP$_4$dG was concentrated to a solid, then co-evaporated 6–7 times with water to yield the ammoniu salt of the dinucleotide as an orange-yellow solid (140 mg, estimated purity by HPLC (AUC) 94%).

EXAMPLE 18

P$^1$-(2'-deoxyadenosine 5'-)P$^4$-(uridine 5'-)tetraphosphate (UP$_4$dA)

Reaction of 2'-deoxyadenosine 5'-monophosphate (d-AMP, Sigma, 500 mg) with uridine 5'-cyclic metaphosphate essentially as described above gave UP$_4$dA as the solid white ammonium salt (140 mg, HPLC purity as above, 99%).

EXAMPLE 19

P$^1$-(2'-deoxyinosine 5'-)P$^4$-(uridine 5'-)tetraphosphate (UP$_4$dI)

2'-Deoxyinosine 5'-monophosphate (d-IMP, Sigma, sodium salt 1.0 g) is converted to the free acid form with Dowex 50 (H$^+$) resin as described for UTP above. The eluent is neutralized with tributylamine (2.0 mL) and the mixture concentrated to an oil under vacuum. The resulting tributylamine salt is dried by evaporation with DMF, the residue dissolved in DMF (4.5 mL) and treated with uridine 5'-cyclic trimetaphosphate essentialy as described above to yield P$^1$-(2'-deoxyinosine 5'-)P$^4$-(uridine 5'-)tetraphosphate.

EXAMPLE 20

P$^1$-(2'-deoxycytidine 5'-)P$^4$-(uridine 5'-)tetraphosphate (UP$_4$dC) 2'-Deoxycytidine 5'-monophosphate (d-CMP, Sigma, 500 mg) treated essentially as above yielded P$^1$-(2'-deoxycytidine 5'-)-P$^4$-(uridine 5'-)tetraphosphate as a white solid (130 mg) estimated HPLC purity 82%.

EXAMPLE 21

Pharmacological Activity as Measured by the Inositol Phosphate Assay

The compounds of Examples 1–20 were tested for their ability to elicit P2Y$_1$, P2Y$_2$, P2Y$_4$ and P2Y$_6$ receptor activity using the inositol phosphate assay as described by E. Lazarowski, et al., *Brit. J Pharm.* 116, 1619–27 (1995). The results are summarized in Table II below.

TABLE II

DINUCLEOTIDE ACTIVITY SUMMARY
EC$_{50}$'s ($\mu$mol)

| Example | P2Y1 | P2Y2 | P2Y4 | P2Y6 |
|---|---|---|---|---|
| 1 | IA | WEAK | 11.1 (60%) | IA |
| 2 | IA | 5.71 | 1.0 (80%) | WEAK |
| 3 | 3.67 | 0.63 | 1.19 | 2.56 |
| 4 | IA | 0.02 | n/a | 0.05 (20%) |
| 5 | 31.2 (55%) | 3.8 (80%) | 2.87 | 92.64 |
| 6 | WEAK | 0.46 | 19.8 (75%) | IA |
| 6a | nd | 0.3 | 0.06 | 0.87 |
| 7 | IA | 0.11 | 0.2 | 0.88 |
| 8 | IA | 0.11 | 0.15 | 0.8 |
| 9 | >100 | 0.37 | 4.16 | 1.79 |
| 10 | IA | 0.19 | 0.32 (65%) | 1.3 |
| 11 | IA | 0.13 | 0.38 (75%) | 3.39 |
| 12 | IA | 0.1 | 0.39 | 0.92 |
| 13 | nd | 0.2 | 0.13 | 0.54 |
| 14 | nd | 10.7 | 14.7 | 3.5 |
| 15 | IA | 0.64 | 3.72 | 9.71 |
| 16 | IA | 0.79 | 0.73 | 5.33 |

IA     Response < 2-fold basal
WEAK   EC$_{50}$ > 100 $\mu$mol
(XX%)   Percentage response of same study positive control
nd     not determined The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound selected from the group consisting of:

P$^1$-(Thymidine 5'-)P$^4$-(uridine 5'-)tetraphosphate (UP$_4$T),

P$^1$(Inosine 5'-)P$^4$-(uridine 5'-)tetraphosphate (UP$_4$I),

P$^1$-(4-Thiouridine 5'-)uridine 5'-)tetraphosphate (UP$_4$(4-SH-U)),

P$^1$-(Cytosine β-D-arabinofuranoside 5'-)P$^4$-(uridine 5'-)tetraphosphate (UP$_4$araC), P$^1$-(Uridine 5'-)P$^4$-(xanthosine 5'-)tetraphosphate (UP$_4$X), P$^1$-(2'-deoxyuridine 5'-)P$^4$-(uridine 5'-)tetraphosphate (UP$_4$dU), P$^1$-(3'-Azido-3'-deoxythymidine 5'-)P$^4$-(uridine 5'-)tetraphosphate (UP$_4$(AZT)), P$^1$,P$^4$-Di(3'-azido-3'-deoxythymidine 5'-)tetraphosphate ((AZT)$_2$P$_4$), P$^1$,P$^6$-Di(uridine 5'-)hexaphosphate (U$_2$P$_6$), 2'(3')-Benzoyl-P$^1$,P$^4$-di(uridine 5'-)tetraphosphate, P$^1$,P$^4$-Di(2'(3')-benzoyluridine 5'-)tetraphosphate, P$^1$-(2'-deoxyguanosine 5'-)P$^4$-(uridine 5'-)tetraphosphate (UP$_4$dG), P$^1$-(2'-deoxyadenosine 5'-)P$^4$-(uridine 5'-)tetraphosphate (UP$_4$dA), P$^1$-(2'-deoxyinosine 5'-)P$^4$-(uridine 5'-)tetraphosphate (UP$_4$dI) and $P^1$-(2'-deoxycytidine 5'-)$P^4$-(uridine 5'-)tetraphosphate ($UP_4dC$).

2. $P^1$(Inosine 5'-)$P^4$-(uridine 5'-)tetraphosphate.

3. $P^1$-(2'-deoxycytidine 5'-)$P^4$-(uridine 5'-)tetraphosphate.

4. A method of treating mucus secretions associated with chronic obstructive pulmonary diseases in a mammal by administering an amount of a compound of claim 1 effective to treat mucus secretions associated with chronic obstructive pulmonary diseases.

5. A method of treating sinusitis, otitis media or nasolacrimal duct obstruction in a mammal by administering an effective mucus secretion clearing amount of a compound of claim 1.

6. A method of treating dry eye in a mammal by administering an effective dry eye treatment amount of a compound of claim 1.

7. A method of treating retinal detachment in a mammal by administering an effective retinal detachment treatment amount of a compound of claim 3.

8. A method of facilitating sputum induction in a mammal by administering an amount of a compound of claim 1 effective to facilitate sputum induction.

9. A method of facilitating expectoration in a mammal by administering an amount of a compound of claim 1 effective to facilitating expectoration.

* * * * *

UNITED STATES PATENT AND TRADEMARK OFFICE
CERTIFICATE OF CORRECTION

PATENT NO.    : 6,348,589 B1                                        Page 1 of 1
DATED         : February 19, 2002
INVENTOR(S)   : Pendergast et al.

It is certified that error appears in the above-identified patent and that said Letters Patent is hereby corrected as shown below:

Title page,
Item [63], Related U.S. Application Data, change "now Pat. No. 5,900,407" to -- now Pat. No. 5,837,861 --; and after "1997", insert -- , now Pat. No. 5,900,407 --.

Column 1,
Lines 6-10, change "which is cont-in-part of U.S. Ser. No. 08,797,472 filed Feb. 6, 1997 which is a continuation-in-part application of U.S. Ser. No. 08/798,508 filed Feb. 10, 1997, now U.S. Patent No. 5,900,407" to -- ; which is a continuation-in-part application of U.S. Application No. 08/798,508, filed Feb. 10, 1997, now U.S. Patent No. 5,837,861; which is a continuation-in-part application of U.S. Application No. 08/797,472, filed Feb. 6, 1997, now U.S. Patent No. 5,900,407 --.

Column 6,
Line 60, change "I" to -- III --.

Column 7,
Line 2, change "III" to -- II --.

Signed and Sealed this

First Day of April, 2003

JAMES E. ROGAN
*Director of the United States Patent and Trademark Office*

Disclaimer 6,348,589—William Pendergast, Durham; Benjamin R. Yerxa, Raleigh; Janet L. Rideout, Raleigh; Suhaib M. Siddiqi, Raleigh, all of NC. CERTAIN DINUCLEOTIDES AND THEIR USE AS MODULATORS OF MUCOCILIARY CLEARANCE AND CILLIARY BEAT FREQUENCY. Patent dated February 19, 2002. Disclaimer filed April 1, 2003, by the assignee, Inspire Pharmaceuticals, Inc.

The term of this patent shall not extend beyond the expiration date of Pat. No. 5,837,861.

*(Official Gazette, July 15, 2003)*